(12) United States Patent
Hsu et al.

(10) Patent No.: US 11,051,758 B2
(45) Date of Patent: Jul. 6, 2021

(54) ELECTRONIC DEVICE CAPABLE OF DETECTING WEARING STATE OR TOUCHING STATE

(71) Applicant: PixArt Imaging Inc., Hsin-Chu (TW)

(72) Inventors: Che-Chia Hsu, Hsin-Chu (TW); Jian-Cheng Liao, Hsin-Chu (TW); Yu-Han Chen, Hsin-Chu (TW); Chi-Chieh Liao, Hsin-Chu (TW)

(73) Assignee: PixArt Imaging Inc., Hsin-Chu (TW)

(*) Notice: Subject to any disclaimer, the term of this patent is extended or adjusted under 35 U.S.C. 154(b) by 0 days.

(21) Appl. No.: 16/591,651

(22) Filed: Oct. 3, 2019

(65) Prior Publication Data
US 2021/0100502 A1   Apr. 8, 2021

(51) Int. Cl.
*A61B 5/00* (2006.01)
*G04G 21/02* (2010.01)
*H03K 17/955* (2006.01)
*G06F 1/16* (2006.01)

(52) U.S. Cl.
CPC ........... *A61B 5/681* (2013.01); *G04G 21/025* (2013.01); *H03K 17/955* (2013.01); *G06F 1/163* (2013.01)

(58) Field of Classification Search
CPC .... A61B 5/681; G04G 21/025; H03K 17/955; G06F 1/163
See application file for complete search history.

(56) References Cited

U.S. PATENT DOCUMENTS

| | | | |
|---|---|---|---|
| 2015/0070297 A1* | 3/2015 | Mao | G06F 3/046 345/174 |
| 2017/0332236 A1* | 11/2017 | Li | G06F 21/32 |
| 2017/0366655 A1* | 12/2017 | Thompson | H04W 4/70 |

* cited by examiner

*Primary Examiner* — Nader Bolourchi
(74) *Attorney, Agent, or Firm* — Winston Hsu

(57) ABSTRACT

A wearable electronic device with a function of detecting a wearing state, comprising: at least one electrode; a capacitance calculating circuit, coupled to the electrode, configured to calculate a capacitance variation generated by at least one of the electrode; and a wearing state determining circuit, coupled to the capacitance calculating circuit, configured to determine the wearing state according to the capacitance variation. By this way, the wearing state can be auto detected and the wearable electronic device can be correspondingly control according to the wearing state.

12 Claims, 7 Drawing Sheets

ELECTRONIC DEVICE CAPABLE OF DETECTING WEARING STATE OR TOUCHING STATE

BACKGROUND OF THE INVENTION

1. Field of the Invention

The present invention relates to an electronic device capable of detecting a wearing state or a touching state, and particularly relates to an electronic device having at least one electrode to detect a wearing state or a touching state.

2. Description of the Prior Art

In recent years, a smart wearable electronic device such as a smart watch or a smart wristband has become more and more popular. Such smart wearable electronic device always has various functions, such as mobile payment or biological information detection (e.g. blood pressure, heart rate). However, the biological information detection may fail or non-accurate if the user does not wear the smart wearable electronic device in a proper manner. Also, the smart wearable electronic device always needs to be recognized before using the mobile payment. However, if the smart wearable electronic device is stolen after being recognized, someone who steals it can use this device to pay any bill. However, no security mechanism is provided to avoid such issue.

SUMMARY OF THE INVENTION

Therefore, one embodiment of the present invention is to provide a wearable electronic device with a function of detecting a wearing state.

Another embodiment of the present invention is to provide an electronic device with a function of detecting a touch state and integrate electrodes to at least one port of the electronic device.

One embodiment of the present invention is to provide a wearable electronic device with a function of detecting a wearing state, comprising: at least one electrode; a capacitance calculating circuit, coupled to the electrode, configured to calculate a capacitance variation generated by at least one of the electrode; and a wearing state determining circuit, coupled to the capacitance calculating circuit, configured to determine the wearing state according to the capacitance variation.

Another embodiment of the present invention is to provide an electronic device capable with a function of detecting a touch state, comprising: at least one electrode; a capacitance calculating circuit, coupled to the electrode, configured to calculate a capacitance variation generated by at least one the electrode; and a touch state determining circuit, coupled to the capacitance calculating circuit, configured to determine the touch state according to the capacitance variation. The electrode also serves as at least one of following ports of the electronic device: a data port configured to receive data, and a charging port configured to receive a charging voltage.

In view of above-mentioned embodiments, a wearing state or a touch state of the electronic device can be detected via electrodes of the electronic device, thus the problem caused by an improper wearing manner can be improved. Also, the present invention provides a more strict security mechanism according to the wearing state. Besides, the integration of the ports and the electrodes can reduce the size of the electronic device.

These and other objectives of the present invention will no doubt become obvious to those of ordinary skill in the art after reading the following detailed description of the preferred embodiment that is illustrated in the various figures and drawings.

DETAILED DESCRIPTION

In following descriptions, a plurality of embodiments are provided to explain the concept of the present invention. Please note the components in following embodiments can be implemented by hardware (e.g. circuit or device), or implemented by firmware (e.g. a processor installed with at least one program). Also, the components in each embodiment can be integrated to fewer components, or be divided to more components.

Additionally, in following embodiments, a smart watch is taken as an example to explain the concepts of the present invention. However, the wearable electronic device is not limited to a smart watch. Furthermore, the concept disclosed by the present invention can be applied any other kind of electronic device to detect a touch state or a wearing state of the electronic device.

Figure 1:
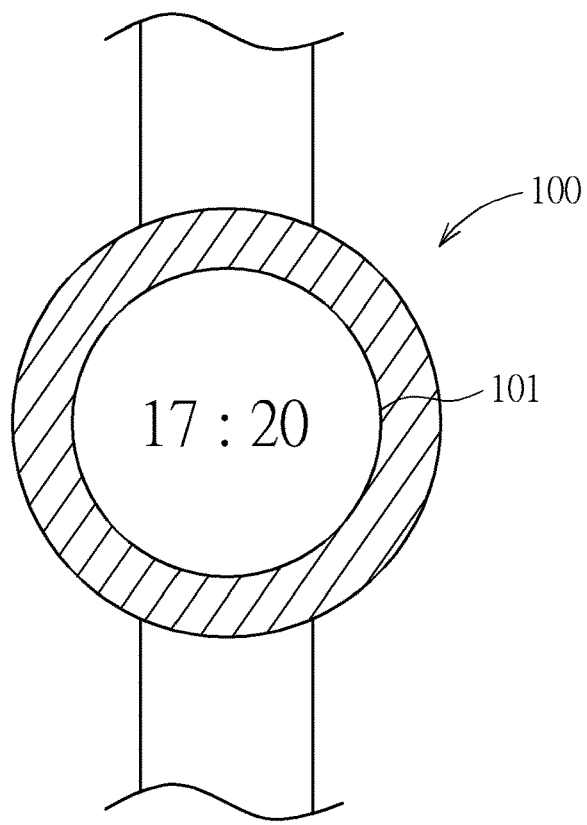
FIG. 1 and FIG. 2 are schematic diagrams illustrating a smart watch according to one embodiment of the present invention.
Figure 2:
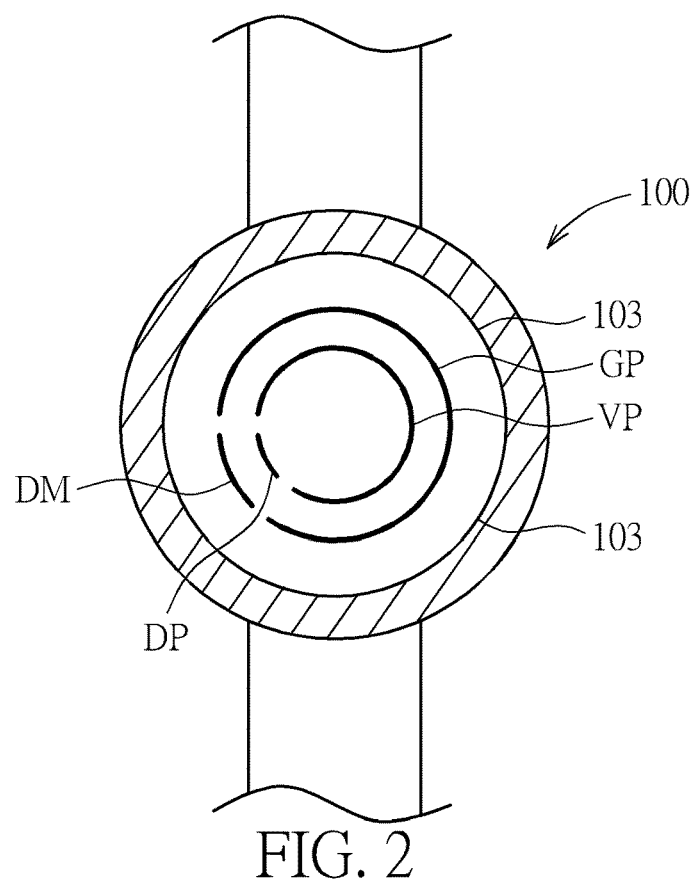

FIG. 1 and FIG. 2 are schematic diagrams illustrating a smart watch 100 according to one embodiment of the present invention. As illustrated in FIG. 1, the smart watch 100 comprises a front surface 101 which can show desired information such as time, messages, or images, such as a display. In FIG. 2, the smart watch 100 comprises a sensing surface 103 which is a back surface of the smart watch 100 in this embodiment, by which a user can cause the capacitance variation to the electrode included in the smart watch 100 when the user wears the smart watch 100. However, the sensing surface 103 can be any other surface of an electronic device if the concept of the present invention is applied to another type of electronic device.

In some embodiments, the sensing surface 103 can comprise a plurality of electrodes. Such electrodes can be mutual capacitance electrodes or self-capacitance electrodes. If the electrode is a mutual capacitance electrode, the electrode only serves as one of a transmitter (TX) and a receiver (RX). If the electrode is a self-capacitance capacitance electrode, it serves as a transmitter (TX) and a receiver (RX). In one embodiment, a USB interface comprising at least one data port, a voltage port and a ground port is applied as the electrodes. Further, in one embodiment, the electrodes are ring shapes. Via such shape, the wearing state for the smart watch 100 in various directions can be detected. These examples will be described for more details in following descriptions.

In the embodiment of FIG. 2, a USB interface comprising data port DM, DP, a voltage port VP and a ground port GP is applied as the electrodes. The USB interface could be used to transmit signals between the smart watch 100 and an external device and to charge the smart watch 100 while the USB interface is connected to a USB cable. The USB interface, while disconnected from the USB cable, could be used to detect a wearing state or a touching state of the smart watch 100.

Please refer to FIG. 2, the sensing surface 103 comprises a data port DM configured to receive negative signals from inside of the smart watch 100 and a data port DP configured to receive positive signals from inside of the smart watch 100. The negative signal and the positive signal can form a differential signal. Also, the sensing surface 103 further comprises a charging port comprising a voltage port VP configured to receive a charging voltage, and a ground port GP coupled to a ground voltage level. Please note, the smart watch 100 can comprise other types of the charging port and data ports. In following embodiments, at least one of the data ports DM, DP, the voltage port VP and the ground port GP can also serve as electrodes. Related descriptions will be illustrated for more detail later.

More specifically, the data ports DM, DP, the voltage port VP and the ground port GP form two concentric circles, in another embodiment, the four ports could form four concentric circles respectively. The inner circle is formed by the data port DP and the voltage port VP, and the outer circle is formed by the data port DM and the ground port GP. When at least two ports form one circle, then the circle has to be separated in at least two sections and each section is coupled to one port. The four ports should not be connected together to avoid short circuit. If two electrodes formed by data ports DM, DP, the voltage port VP or the ground port GP serve as mutual capacitance electrodes, one port in the inner circuit and one port in the outer circuit form mutual capacitances there between. Take FIG. 6 for example, the data port DM and the data port DP form mutual capacitances there between.

Figure 3:
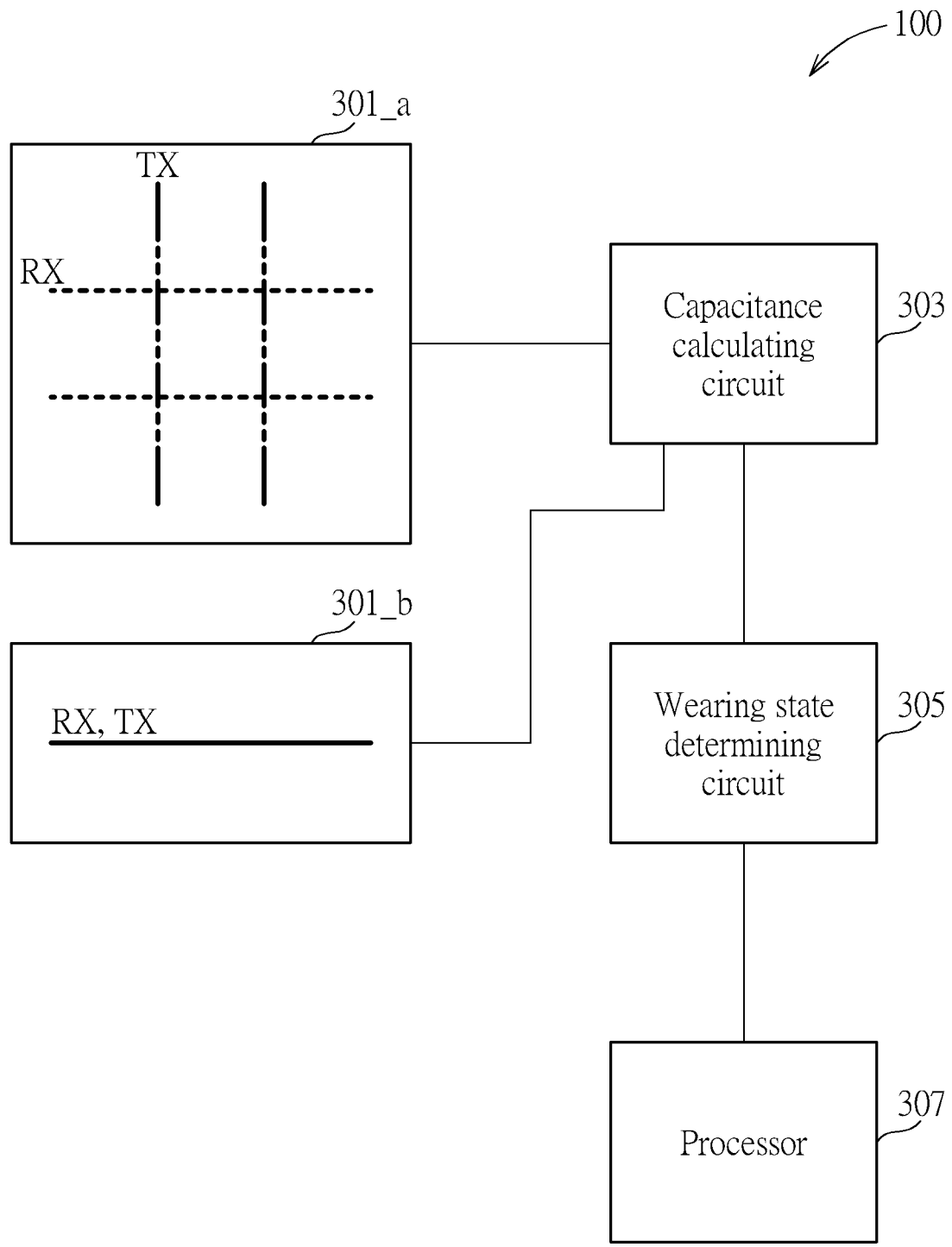
FIG. 3 is a block diagram illustrating a smart watch according to one embodiment of the present invention.

FIG. 3 is a block diagram illustrating a smart watch 100 according to one embodiment of the present invention. As illustrated in FIG. 3, the smart watch 100 comprises at least one electrode (301_a or 301_b), a capacitance calculating circuit 303 and a wearing state determining circuit 305. The capacitance calculating circuit 303 is configured to calculate a capacitance variation generated by at least one the electrode. The wearing state determining circuit 305 is configured to determine the wearing state according to the capacitance variation. In one embodiment, the wearing state comprises a worn state and a taken off state. The worn state means the smart watch 100 is worn by a user in a proper manner such that the biological information can be measured correctly, and the taken off state means the smart watch 100 is not worn by the user or worn in a proper manner.

The wearing state determining circuit 305 can determine whether the smart watch 100 is in the worn state or the taken off state according to the capacitance variation. For example, when the user wears the smart watch 100 in a proper manner, the capacitance calculating circuit 303 calculates that the electrode(s) has (have) a first capacitance value. Also, when the user takes off the smart watch 100, the capacitance calculating circuit 303 calculates that the electrode(s) has (have) a second capacitance value. Therefore, the wearing state determining circuit 305 can determine whether the smart watch 100 is in the worn state or the taken off state according to the capacitance variation between the first capacitance value and the second capacitance value. Please note, the wearing state can be defined to have other states rather than the worn state and the taken off state, for example a state indicates the smart watch 100 is not worn in a proper manner or a state indicates the smart watch 100 is laid on a desk. Further the wearing state can be regarded as one kind of a touch state, therefore the concepts disclosed by the present invention can be applied to detect a touch state.

The electrode can be the mutual capacitance electrode 301_a or the self-capacitance electrode 301_b. The mutual capacitance electrode 301_a means one electrode only serves one of a transmitter (TX) and a receiver (RX). Also, the self-capacitance electrode 301_b means a single electrode serves as a transmitter (TX) and a receiver (RX). Therefore, if the electrode is the mutual capacitance electrode 301_a, the capacitance calculating circuit 303 calculates capacitance variation between different electrodes. Further, if the electrode is the self-capacitance electrode 301_b, the capacitance calculating circuit 303 calculates capacitance variation of a single electrode. Details of the mutual capacitance electrode 301_a and the self-capacitance electrode 301_b are well known by persons skilled in the art, thus are omitted for brevity here.

Figure 4:
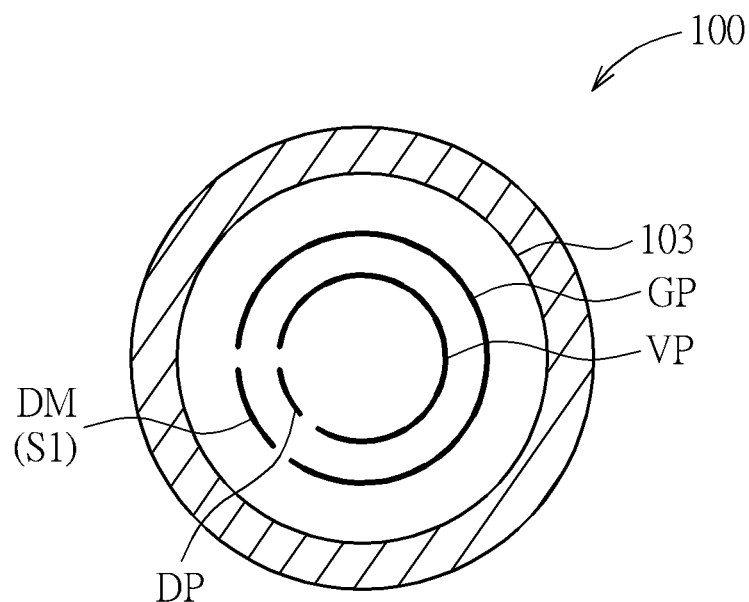
FIG. 4-FIG. 11 are schematic diagrams illustrating smart watches according to different embodiments of the present invention.
Figure 5:
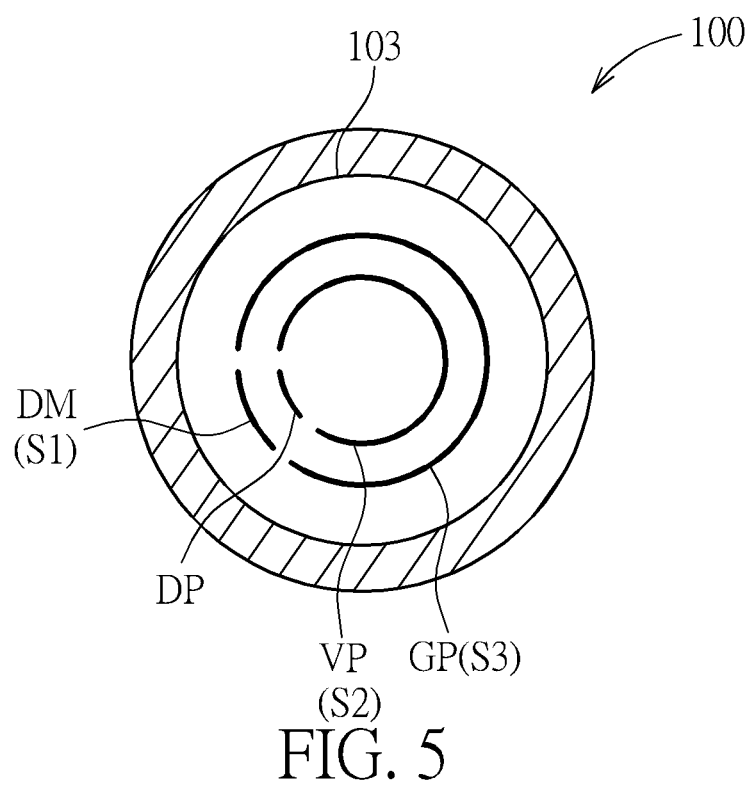

As above-mentioned, the sensing surface 103 of the smart watch 100 comprises data ports DM and DP, the voltage port VP and the ground port GP. In following embodiments, at least one of the data ports DM and DP, the voltage port VP and the ground port GP serves as the transmitter and/or the receiver. As illustrated in FIG. 4, the data port DM serves as a self-capacitance electrode S1. Also, one port is not limited to serve as only one self-capacitance electrode. For example, in the embodiment of FIG. 5, the data port DM serves as a self-capacitance electrode S1, the voltage port VP serves as a self-capacitance electrode S2 and the ground port GP serves as a self-capacitance electrode S3. By such structure or similar structure, the capacitance variations in different directions can be detected since the self-capacitance electrodes are disposed to cover different directions.

In one embodiment, at least partial of the electrode exposes outside the sensing surface 103 such that the user can cause capacitance variation via the exposed electrode(s). Further, in one embodiment, the sensing surface 103 covers the electrode but the user still can cause the capacitance variation to the electrode(s) when the user non-directly touches the electrode. For example, the user can cause the capacitance variation to the electrode (s) when the user wears the smart watch 100. Such structure can also be applied to following embodiments.

Figure 6:
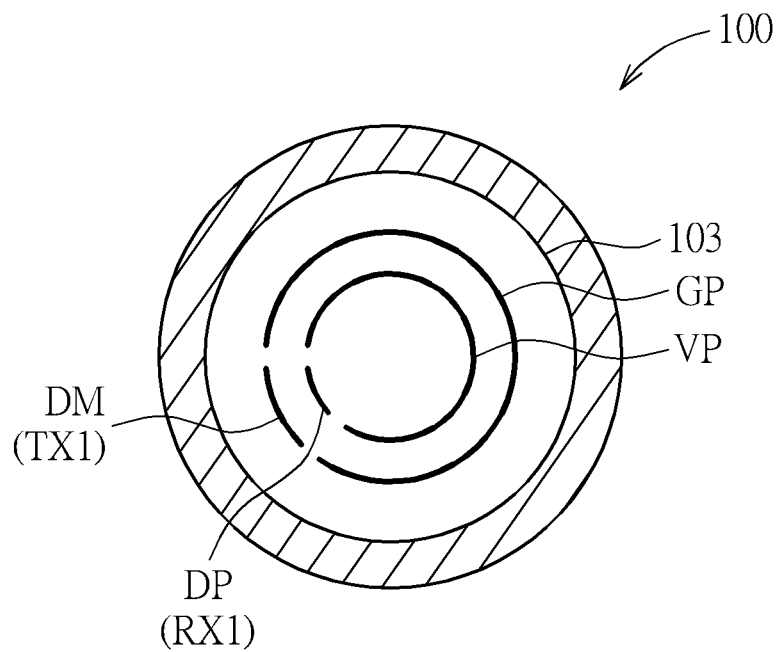
Figure 7:
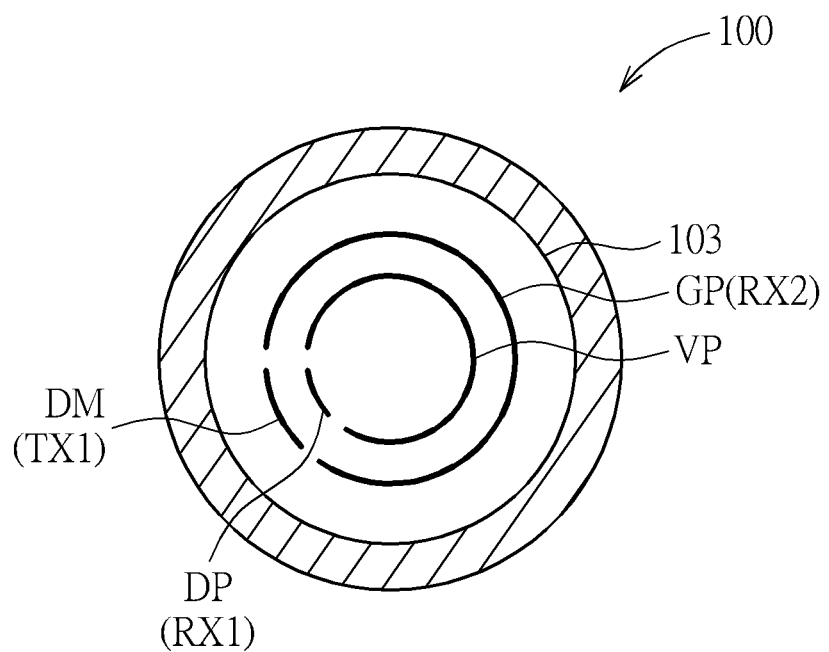

Besides, at least two of the data ports DM and DP, the voltage port VP and the ground port GP can serve as mutual-capacitance electrodes. FIG. 6 and FIG. 7 illustrate the embodiments that the ports of the smart watch 100 serve as mutual capacitance electrodes. In following descriptions, a TX electrode means a mutual capacitance electrode serving as a transmitter, and a RX electrode means a mutual capacitance electrode serving as a receiver. For example, in the embodiment of FIG. 6, the data port DM is a TX electrode TX1, and the data port DP is a RX electrode RX1. However, the smart watch provided by the present invention can have more than one group of transmitter and receivers, rather than limited on one group of transmitter and receiver illustrated in FIG. 6. For example, the voltage port and the ground port can serve as another group of transmitter and receiver.

Further, a group of transmitter and receiver is not limited to one transmitter and one receiver. In the embodiment of FIG. 7, the data port DM is a TX electrode TX1, the data port DP is a RX electrode RX1, and the ground port GP is a RX electrode RX2. That is, a group of transmitter and receiver can have X transmitter(s) and Y receiver(s), wherein X and Y are positive integers equal or larger than 1.

In one embodiment, only one of the TX electrode transmits a driving signal when the RX electrodes receives a corresponding sensing signal. For more detail, when the TX electrode receives the driving signal, the corresponding sensing signal is generated to the RX electrode due to coupling capacitance between the TX electrode and the RX electrode. The driving signal can be, for example, generated by the capacitance calculating circuit 303.

Take the embodiment in FIG. 7 for example, only the TX electrode T1 transmits a driving signal when the RX electrodes RX1, RX2 receive corresponding sensing signals, even if the smart watch 100 comprises any other TX electrode. The sensing signals of different RX electrodes may vary corresponding to the distances between the TX electrode T1 and the RX electrodes RX1, RX2, or vary corresponding to effective areas between the TX electrode T1 and the RX electrodes RX1, RX2. The effective area means a region which the above-mentioned coupling capacitance can generate. In the embodiment of FIG. 7, the effective area between the TX electrode T1 and the RX electrode RX1 is smaller than the effective area between the TX electrode T1 and the RX electrode RX2. In one embodiment, more than one TX electrodes can exist. In such case, the TX electrodes can have different driving signals. However, these different driving signals still have the same frequency.

In the same embodiment, isolation material (e.g. electric varnish) is provided on the RX electrodes RX1, RX2, such that the TX electrode TX1 is exposed and the RX electrodes RX1, RX2 are isolated. By this way, the smart watch 100 can be protected from a short circuit issue when the TX electrode TX1 and the RX electrodes RX1, RX2 simultaneously touch conductive materials such as water or metal. In one embodiment, the isolation material can also be provided to the TX electrode TX1, thus a stricter short circuit protection can be acquired. It will be appreciated that the isolation material can be provided to other embodiments rather than limit to the embodiment of FIG. 7.

In one embodiment, the smart watch 100 can further comprise a processor configured to control the smart watch 100 according to the wearing state, such as the processor 307 in FIG. 3. For example, if the processor 307 detects the smart watch 100 is recognized by the user (e.g. by password or finger print) in a worn state, the processor may switch the smart watch 100 from a recognized state to a non-recognized state when the smart watch 100 changes from the worn state to the taken off state. By this way, the smart watch 100 cannot be used to pay after the user takes off the smart watch 100. The wearing state determining circuit 305 can be integrated to the processor 307.

Figure 8:
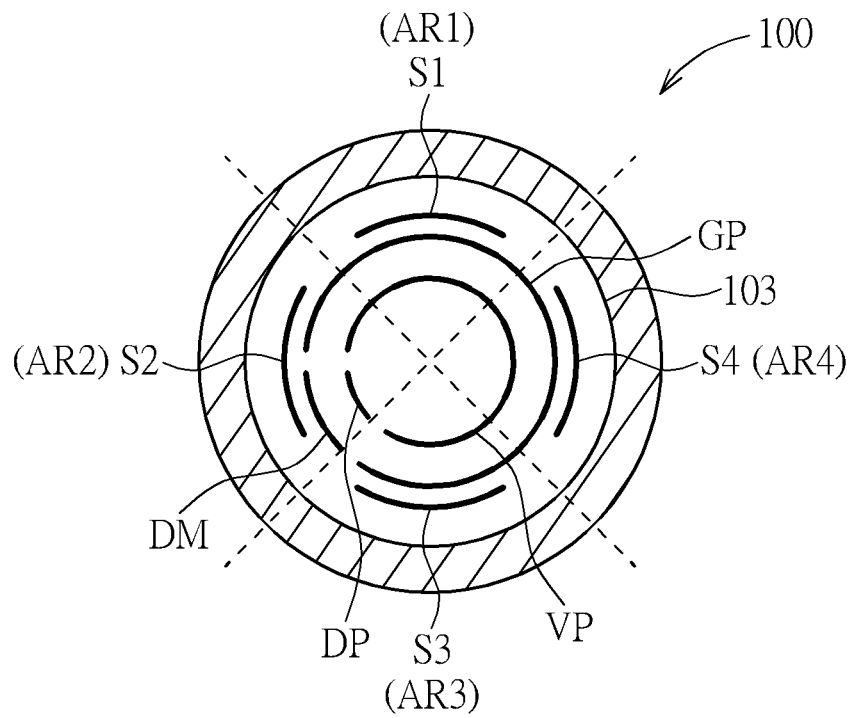
Figure 9:
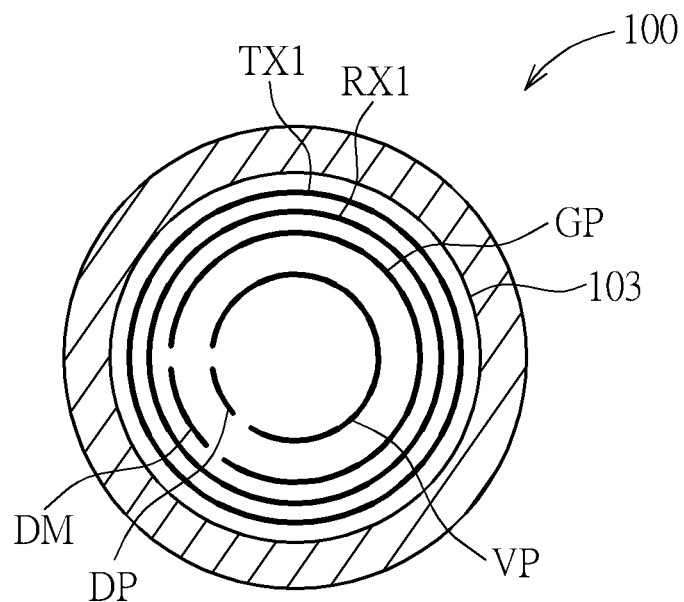

The electrodes can be independent from the port located on the sensing surface 103 rather than integrated to the ports. As illustrated in FIG. 8, the smart watch 100 comprises self-capacitance electrodes S1, S2, S3, S4 independent from the data ports DM, DP, the voltage port VP and the ground port GP. Further, in the embodiment of FIG. 9, the smart watch 100 comprises a TX electrode TX1 and a RX electrode RX1 independent from the data ports DM, DP, the voltage port VP and the ground port GP.

Figure 10:
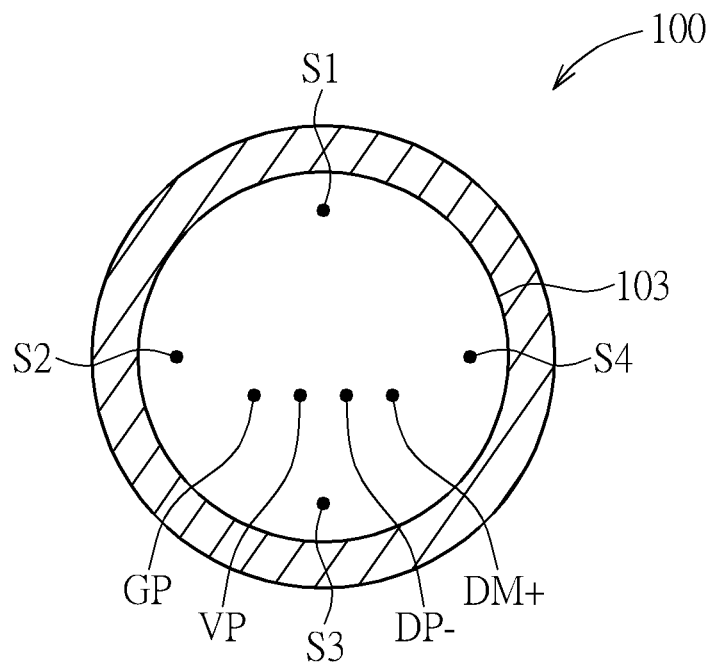
Figure 11:
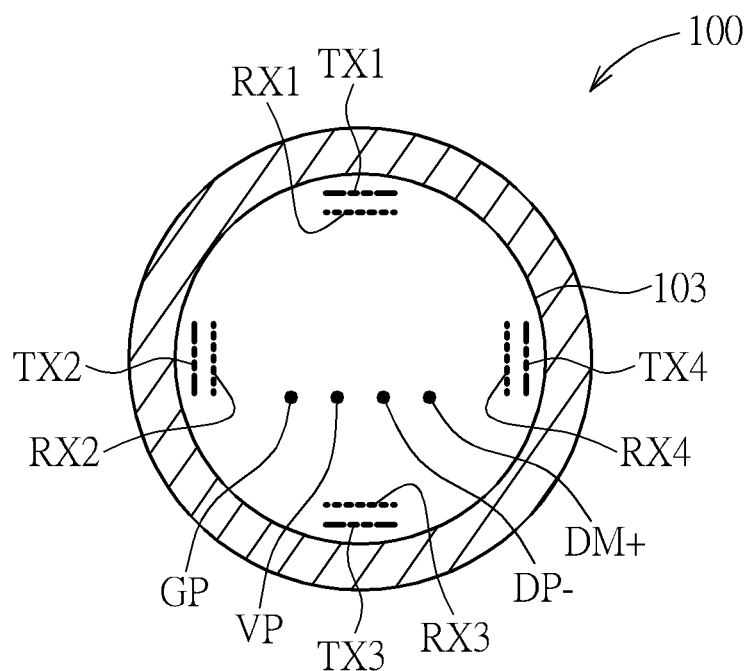

Besides, the locations and the shapes of the ports and the electrodes are not limited to above-mentioned embodiments. For example, as illustrated in FIG. 10, the data ports DM, DP, the voltage port VP, the ground port GP and the self-capacitance electrodes S1, S2, S3, S4 are point shapes. Also, in the embodiment of FIG. 11, the data ports DM, DP, the voltage port VP, the ground port GP are point shapes, and the TX electrodes TX1, TX2, TX3, TX4, the RX electrodes RX1, RX2, RX3, RX4 are line shapes. It will be appreciated that the smart watch 100 is not limited to comprise the electrodes while comprising other ports on the sensing surface 103. The smart watch 100 can comprise only the electrodes while comprising no other ports on the sensing surface 103.

Figure 12:
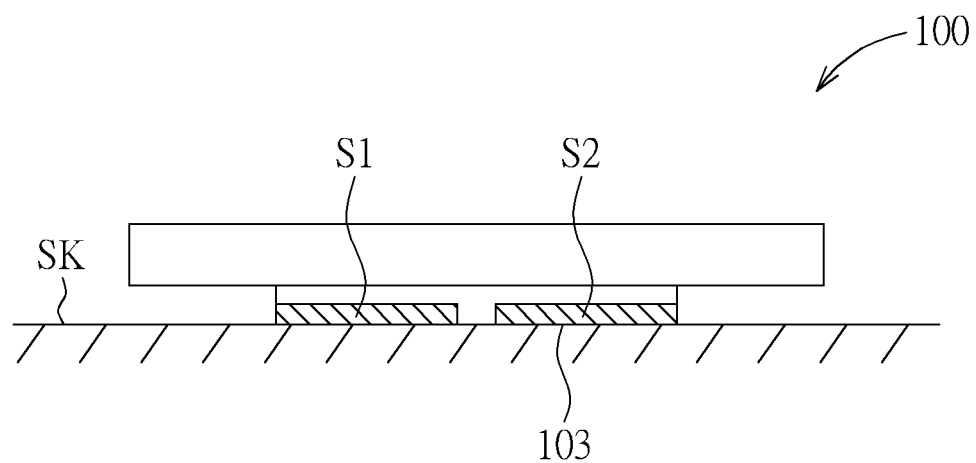
FIG. 12-FIG. 13 are schematic diagrams illustrating examples of determining a wearing state of the smart watch.
Figure 13:
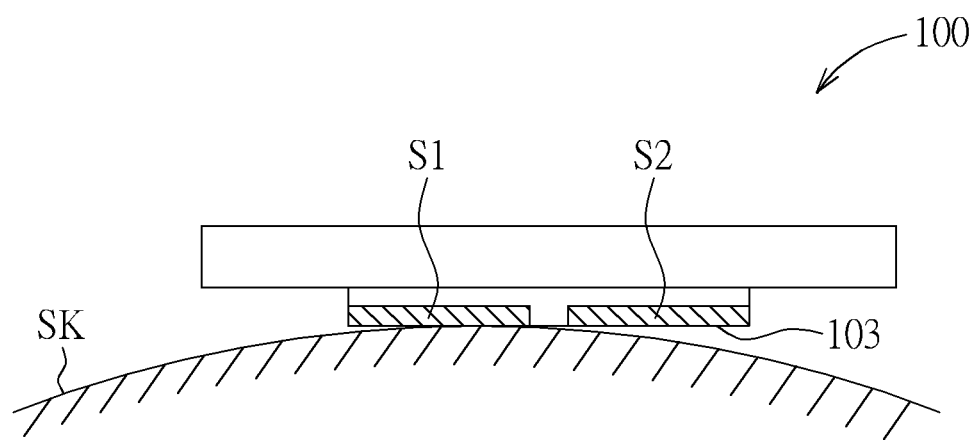

FIG. 12-FIG. 13 are schematic diagrams illustrating examples of determining a wearing state of the smart watch. In this embodiment, the wearing state determining circuit 305 determines the wearing state according to a location of the electrode which is touched. In these embodiments, the smart watch 100 comprises self-capacitance electrodes S1 and S2, but not limited.

As illustrated in FIG. 12, the skin SK of a user touches the self-capacitance electrodes S1 and S2 when the user properly wears the smart watch 100. Therefore, the wearing state determining circuit 305 determines the wearing state is a worn state when the self-capacitance electrodes S1 and S2 are touched. Further, in the embodiment of FIG. 13, the user does not wear the smart watch 100 properly, thus only the self-capacitance electrode S1 is touched by the skin SK. Accordingly, the wearing state determining circuit 305 determines the wearing state is a taken off state when only one of the self-capacitance electrodes S1 and S2 is touched, or none of them is touched. In one embodiment, the smart watch can generate some inform messages such as light or audible messages to inform the user that the smart watch 100 is in a taken off state.

In one embodiment, the electrodes can be provided in a plurality of angle regions (or named Quadrants). Take FIG. 8 in example, the self-capacitance electrode S1, S2, S3 and S4 are respectively provided in different angle regions AR1, AR2, AR3 and AR4. The wearing state determining circuit 305 can determine the wearing state according to the capacitance variations of the angle regions AR1-AR4. In such embodiment, the angle regions AR1-AR4 can have one of the two states: a normal state or an error state. The normal state means the capacitance variations of the angle region indicate the electrode(s) in the angle region touches or closely touches the skin of a user. On the opposite, the error state means the capacitance variations of the angle region indicate the electrode(s) in the angle region does not touch or does not closely touch the skin of a user. Therefore, in one embodiment, the wearing state determining circuit 305 determines a wearing state according to a number of the angle region (s) which operate in the error state. For example, in the embodiment of FIG. 8, the wearing state determining circuit 305 determines the smart watch 100 is worn in an improper manner if two or more than two of the angle regions AR1-AR4 have the error state. On the opposite, the wearing state determining circuit 305 determines the smart watch 100 is worn in a proper manner if less than two of the angle regions AR1-AR4 have the error state.

Further, in one embodiment, the angle region is determined to operate in the error state if more than a predetermined number of electrodes in the angle region have capacitance variation indicating the electrode in the angle region does not touch or does not closely touch the skin of a user. For example, in the embodiment of FIG. 8, if the angle region AR1 has three electrodes and two or more than two of the electrodes therein have capacitance variation indicating the electrode in the angle region does not touch or does not closely touch the skin of a user, the angle region AR1 is determined to have the error state. On the opposite, if less than two of the electrodes therein have capacitance variation indicating the electrode in the angle region does not touch or does not closely touch the skin of a user, the angle region AR1 is determined to have the normal state.

Please note, the above-mentioned embodiments using "angle region" is not limited to be applied to the case that the electrodes are self-capacitance electrodes. The embodiments using "angle region" can also be applied to the case that the electrodes are mutual capacitance electrodes. Further, the numbers (two, three) in above-mentioned embodiments using "angle region" is only for example, but do not mean to limit the scope of the present invention.

In view of above-mentioned embodiments, a wearing state of the electronic device can be detected via electrodes of the electronic device, thus the problem caused by an improper wearing manner can be improved. Also, the present invention provides a more strict security mechanism according to the wearing state. Besides, the integration of the ports and the electrodes can reduce the size of the electronic device.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A wearable electronic device with a function of detecting a wearing state, comprising:
   at least one electrode;
   a capacitance calculating circuit, coupled to the at least one electrode, configured to calculate a capacitance variation generated by the at least one electrode;
   a wearing state determining circuit, coupled to the capacitance calculating circuit, configured to determine the wearing state according to the capacitance variation; and
   a sensing surface, by which a user can cause the capacitance variation generated by the at least one electrode when the user wears the wearable electronic device;
   wherein the at least one electrode is provided in a plurality of angle regions of the sensing surface, and the wearing state determining circuit determines the wearing state according to the capacitance variation generated by the at least one electrode in the plurality of angle regions.

2. The wearable electronic device of claim 1, wherein the wearable electronic device comprises a front surface which can show desired information, and comprises a back surface served as the sensing surface.

3. The wearable electronic device of claim 1, wherein the sensing surface covers the at least one electrode and the user can cause the capacitance variation generated by the at least one electrode when the user non-directly touches the at least one electrode.

4. The wearable electronic device of claim 1, wherein at least partial of the at least one electrode exposes outside the sensing surface.

5. The wearable electronic device of claim 4, further comprising isolation material provided on at least part of the exposed partial of the at least one electrode.

6. The wearable electronic device of claim 1, wherein the at least one electrode also serves as at least one of following ports of the wearable electronic device: a data port configured to receive data, and a charging port configured to receive a charging voltage.

7. The wearable electronic device of claim 6, wherein the data port and the charging port form a USB port.

8. The wearable electronic device of claim 1, wherein the wearing state comprises a worn state and a taken off state, wherein the wearable electronic device further comprises a processor configured to control the wearable electronic device to switch from a recognized state to a non-recognized state when the wearable electronic device changes from the worn state to the taken off state.

9. The wearable electronic device of claim 1, wherein the at least one electrodes comprises at least one TX electrode and a plurality of RX electrodes, wherein only one of the at least one TX electrode transmits a sensing signal when the RX electrodes receive the sensing signal.

10. The wearable electronic device of claim 1, wherein the wearing state determining circuit determines the wearing state according to a number of the plurality of angle regions which have an error state, wherein at least one of the plurality of angle regions is determined to operate in the error state when more than a predetermined number of the at least one electrode in the plurality of angle regions have the capacitance variation generated by the at least one electrode, which indicates the at least one electrode in the plurality of angle regions does not touch or does not closely touch skins of the user.

11. The wearable electronic device of claim 10, wherein the wearing state determining circuit determines the wearable electronic device is in a taken off state if a number of the plurality of angle regions which are determined to operate in the error state is more than a predetermined number.

12. A wearable electronic device with a function of detecting a wearing state, comprising:
   at least one electrode;
   a capacitance calculating circuit, coupled to the at least one electrode, configured to calculate a capacitance variation generated by at least one of the at least one electrode; and
   a wearing state determining circuit, coupled to the capacitance calculating circuit, configured to determine the wearing state according to the capacitance variation;
   wherein the at least one electrode also serves as at least one of following ports of the wearable electronic device: a data port configured to receive data, and a charging port configured to receive a charging voltage, wherein the data port and the charging port form a USB port.

* * * * *